United States Patent [19]

Takigawa et al.

[11] Patent Number: 5,053,517
[45] Date of Patent: Oct. 1, 1991

[54] PROCESS FOR PREPARING PYRAZOLECARBOXYLIC ACID COMPOUNDS

[75] Inventors: Shinichiro Takigawa; Shuzo Shinke, both of Funabashi, Japan

[73] Assignee: Nissan Chemical Industries, Ltd., Tokyo, Japan

[21] Appl. No.: 367,428

[22] Filed: Jun. 16, 1989

[30] Foreign Application Priority Data

Jul. 4, 1988 [JP] Japan .................. 63-166274

[51] Int. Cl.$^5$ .................. C07D 401/00; C07D 231/14; C07D 51/16
[52] U.S. Cl. .................. 548/376; 548/377; 548/378; 546/279
[58] Field of Search .................. 548/376, 377, 378; 546/279; 562/412, 409

[56] References Cited

U.S. PATENT DOCUMENTS

| | | | |
|---|---|---|---|
| 3,692,828 | 9/1972 | Onopchenko et al. | 562/412 |
| 3,760,009 | 9/1973 | Suzuki | 562/412 |
| 4,623,726 | 11/1986 | Daniels | 562/409 |
| 4,794,195 | 12/1988 | Hayashi et al. | 562/412 |

*Primary Examiner*—Mary C. Lee
*Assistant Examiner*—Joseph K. McKane
*Attorney, Agent, or Firm*—Frishauf, Holtz, Goodman & Woodward

[57] ABSTRACT

There is disclosed a process for preparing a pyrazolecarboxylic acid derivative represented by the formula (II):

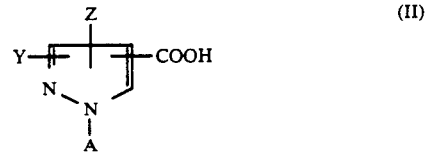

wherein Y and Z each represent a hydrogen atom, a halogen atom, a nitro group, a cyano group, $COOR_1$, $NR_1R_2$, $CONR_1R_2$, $SR_1$, $SO_2NR_1R_2$, $SO_2R_3$, $R_3CO$, $OR_4$, $CHX_2$ or $CX_3$; A represents a hydrogen atom, an alkyl group having 1 to 4 carbon atoms, a substituted or unsubstituted phenyl group, a substituted or unsubstituted pyridyl group or $OR_5$; where $R_1$ and $R_2$ each represent a hydrogen atom or an alkyl group having 1 to 10 carbon atoms; $R_3$ represents an alkyl group having 1 to 10 carbon atoms; $R_4$ represents a hydrogen atom, an alkyl group having 1 to 10 carbon atoms, a substituted or unsubstituted phenyl group, $CHF_2$, $CF_3$ or $CF_3CH_2$; $R_5$ represents an alkyl group having 1 to 10 carbon atoms; and X represents a halogen atom, which comprises oxidizing a pyrazole compound represented by the formula (I):

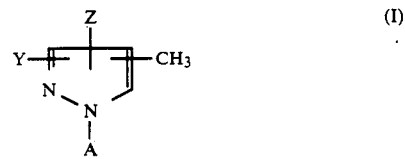

wherein Y, Z and A have the same meanings as defined above, with an oxygen-containing gas in the presence of a metal compound catalyst.

23 Claims, No Drawings

PROCESS FOR PREPARING PYRAZOLECARBOXYLIC ACID COMPOUNDS

BACKGROUND OF THE INVENTION

1. Field of The Invention

This invention relates to a novel method for preparing pyrazolecarboxylic acid derivatives which are useful as an intermediate of a herbicide, etc.

2. Background of The Invention

Heretofore, as the method for preparing pyrazolecarboxylic acid from alkylpyrazole derivatives, it has been known the permanganic acid oxidation method.

However, this method uses excessive amount of permanganate and the yield is extremely bad as 40% or lower.

Also, it is required to process a large amount of waste water and waste material containing manganese so that it is difficult to employ the method as an industrial scale preparation.

Also, as the preparative method of heterocyclic carboxylic acid due to the liquid phase autoxidation method, the following has been known.
(1) Japanese Patent publication No. 9868/1959
(2) Japanese Patent Publication No. 17068/1975

In the aforesaid (1), oxidation of a compound having pyridine or quinoline nucleus has been carried out in the presence of a heavy metal compound such as manganese, cobalt, etc. and a bromine compound.

In the aforesaid (2), oxidation of alkylpyridine derivatives have been carried out in the presence of a compound selected from zirconium, cobalt and manganese and a bromine compound to prepare pyridinecarboxylic acids.

However, it has never been known the method in which only a methyl group of a pyrazole compound having simultaneously a methyl group bonded to the pyrazole ring and a substituent bonded to a nitrogen atom is selectively oxidized to give pyrazolecarboxylic acid derivatives.

SUMMARY OF THE INVENTION

The present inventors have intensively studied concerning the method of obtaining a pyrazolecarboxylic acid derivative from a pyrazole compound having simultaneously a methyl group bonded to the pyrazole ring and a substituent bonded to a nitrogen atom, and as the result, accomplished the present invention.

That is, the present invention concerns a method for preparing a pyrazolecarboxylic acid derivative represented by the formula (II):

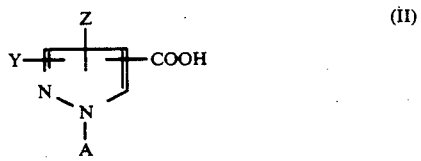

(II)

wherein Y and Z each represent a hydrogen atom, a halogen atom, a nitro group, a cyano group, $COOR_1$, $NR_1R_2$, $CONR_1R_2$, $SR_1$, $SO_2NR_1R_2$, $SO_2R_3$, $R_3CO$, $OR_4$, $CHX_2$ or $CX_3$; A represents a hydrogen atom, an alkyl group having 1 to 4 carbon atoms, a substituted or unsubstituted phenyl group, a substituted or unsubstituted pyridyl group or $OR_5$; where $R_1$ and $R_2$ each represent a hydrogen atom or an alkyl group having 1 to 10 carbon atoms; $R_3$ represents an alkyl group having 1 to 10 carbon atoms; $R_4$ represents a hydrogen atom, an alkyl group having 1 to 10 carbon atoms, a substituted or unsubstituted phenyl group, $CHF_2$, $CF_3$ or $CF_3CH_2$; $R_5$ represents an alkyl group having 1 to 10 carbon atoms; and X represents a halogen atom, which comprises oxidizing a pyrazole compound represented by the formula (I):

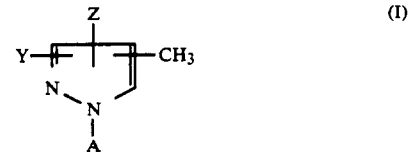

(I)

wherein Y, Z and A have the same meanings as defined above, with an oxygen-containing gas in the presence of a metal compound catalyst.

DESCRIPTION OF THE PREFERRED EMBODIMENTS

In the above formula (II), as the halogen atoms for Y, Z and Z (that is, X in $CHX_2$ or $CX_3$), there may be mentioned a fluorine atom, a chlorine atom, a bromine atom and an iodine atom.

As the alkyl group having 1 to 10 carbon atoms for $R_1$, $R_2$, $R_3$, $R_4$ and $R_5$, there may be mentioned a methyl group, an ethyl group, a n-propyl group, an i-propyl group, a n-butyl group, an i-butyl group, a t-butyl group, a n-pentyl group, an i-pentyl group, a n-hexyl group, an i-hexyl group, a n-heptyl group, an i-heptyl group, a n-octyl group, an i-octyl group, a n-nonyl group, an i-nonyl group, a n-decyl group, an i-decyl group, etc. Among these, as $R_1$ to $R_5$, a methyl group or an ethyl group is particularly preferred.

As the alkyl group having 1 to 4 carbon atoms for A, there may be mentioned a methyl group, an ethyl group, a n-propyl group, an i-propyl group, a n-butyl group, an i-butyl group, a t-butyl group, etc. As A, a methyl group or an ethyl group is particularly preferred.

In the above, n means normal, i means iso and t means tertiary.

The substituents for the substituted or unsubstituted phenyl group and the substituted or unsubstituted pyridyl group may include the above mentioned Y except for a hydrogen atom.

As the oxygen-containing gas, a pure oxygen gas or air may be used.

Oxygen partial pressure may be atmospheric pressure to 80 $kg/cm^2$, preferably atmospheric pressure to 50 $kg/cm^2$.

As the metal compound catalyst, there may be mentioned aliphatic acid iron salts such as iron formate, iron acetate, iron lactate, iron oxalate, iron octylate, etc.; chelate compounds such as iron acetylacetonate, etc.; iron salts such as iron chloride, iron bromide, iron iodide, iron carbonate, iron sulfate, iron nitrate, etc.; aliphatic acid cobalt salts such as cobalt formate, cobalt acetate, cobalt octylate, etc.; chelate compounds such as cobalt acetylacetonate, etc.; cobalt salts such as cobalt chloride, cobalt bromide, cobalt iodide, cobalt carbonate, etc.; aliphatic acid nickel salts such as nickel formate, nickel acetate, nickel octylate, etc.; chelate compounds such as nickel acetylacetonate, etc.; nickel salts such as nickel chloride, nickel bromide, nickel iodide, nickel carbonate, etc.; aliphatic acid manganese salts such as manganese formate, manganese acetate, manganese octylate, etc.; chelate compounds such as manganese acetylacetonate, etc.; manganese salts such as manganese chloride, manganese bromide, manganese iodide, manganese carbonate, etc.; aliphatic acid cerium salts such as cerium formate, cerium acetate, cerium octylate, etc.; chelate compounds such as cerium acetylacetonate, etc.; cerium salts such as cerium chloride, cerium bromide, cerium iodide, cerium carbonate, etc.; aliphatic acid zirconium salts such as zirconium formate, zirconium acetate, zirconium octylate, etc.; chelate compounds such as zirconium acetylacetonate, etc.; zirconium salts such as zirconium chloride, zirconium bromide, zirconium iodide, zirconium carbonate, etc.; copper compounds such as cupric acetate, cupric chloride, cupric carbonate, etc.; palladium compounds such as palladium acetate, palladium chloride, palladium iodide, etc.; osmium compounds such as osmium tetrachloride, etc.; and lead compounds such as lead tetraacetate, etc.

An amount of the metal compound catalyst is not particularly limited, but generally 0.1 to 20 gram-atom, preferably 1 to 10 gram-atom in terms of a metal based on 100 moles of the compound of the formula (I).

Also, the above metal compound catalysts may be used in combination, for example, when 1 to 1/50 gram-atom, preferably 1 to 1/10 gram-atom of manganese is used to cobalt, good results can be obtained.

At least one of a bromine compound, a lithium compound or an alkali metal salt of acetic acid may be used as a reaction promoter.

The bromine compound is not particularly limited and, for example, there may be mentioned ammonium bromide, sodium bromide, potassium bromide, bromine, hydrogen bromide, etc. Sodium bromide or ammonium bromide is particularly preferred. As the lithium compound, there may be mentioned lithium bromide, lithium chloride, lithium fluoride, etc., but lithium chloride is particularly preferred. As the alkali metal salt of acetic acid, there may be mentioned sodium acetate, potassium acetate, lithium acetate, etc., but potassium acetate is particularly preferred.

An amount of the bromine compound is not particularly limited, but generally 0.5 to 20 moles, preferably 1 to 10 moles based on 100 moles of the compound of the formula (I).

The reaction temperature is 20° to 200° C., preferably 60 to 180° C.

The reaction of the present invention may be possible without any solvent but a solvent may be used.

If a solvent is used, operability, safety, and the like are improved.

The solvent is not particularly limited so long as it is stable, and may include a lower aliphatic acid such as acetic acid, propionic acid, a butyric acid, etc.; a lower aliphatic acid anhydride such as acetic anhydride, propionic anhydride, etc., and acetic acid is particularly preferred. An amount of the solvent is not particularly limited, but it is preferred to use 2-fold to 100-fold based on 1 part by weight of the substrate since good results can be obtained.

According to the present invention, the pyrazolecarboxylic acid represented by the formula (II) can be prepared from the pyrazole compound represented by the formula (I) with ease and high yield.

Particularly, the present invention is effective as the method for preparing 3,5-dichloro-1-methylpyrazole-4-carboxylic acid from 3,5-dichloro-1,4-dimethylpyrazole.

The compound is an available compound as an intermediate of a herbicide for corn field.

EXAMPLES

In the following, the present invention will be explained by referring to Examples, but the present invention is not limited by these.

EXAMPLE 1

In a 100 ml of an autoclave made of Hasteroy C-276 were charged 50 ml of acetic acid, 8.25 g (50 mmole) of 3,5-dichloro-1,4-dimethylpyrazole, 0.498 g (2 mmole) of cobalt acetate, 0.123 g (0.5 mmole) of manganese acetate and 0.408 g (4 mmole) of sodium bromide.

After supplying an oxygen gas in the autoclave to make 40 kg/cm$^2$, the mixture was heated under stirring and reaction was carried out at 140° C. for 2 hours.

After the reaction, the products were taken out and analyzed by a gas chromatography, and as the result, a conversion ratio of the starting 3,5-dichloro-1,4-dimethylpyrazole was 100%.

After removing acetic acid, the residue was esterified by dazomethane and the products were analyzed by a gas chromatography-mass spectrograph to obtain the result of M/e being 208 whereby it could be confirmed to be a methyl ester of the objective compound.

As the result of the gas chromatography analysis, a yield of 3,5-dichloro-1-methylpyrazole-4-carboxylic acid was 88.7%.

EXAMPLE 2

In the same manner as in Example 1 except for changing an oxygen pressure to 10 kg/cm$^2$, the reaction and operation were carried out.

A conversion ratio of the starting 3,5-dichloro-1,4-dimethylpyrazole was 90.5% and a yield of 3,5-dichloro-1-methylpyrazole-4-carboxylic acid was 79.9%.

Example 3

In the same manner as in Example 1 except for changing the reaction temperature to 130° C., the reaction and operation were carried out.

A conversion ratio of the starting 3,5-dichloro-1,4-dimethylpyrazole was 95.0% and a yield of 3,5-dichloro-1-methylpyrazole-4-carboxylic acid was 85.0%.

EXAMPLE 4

In the same manner as in Example 1 except for charging 0.392 g (4 mmole) of ammonium bromide in place of sodium bromide, the reaction and operation were carried out.

A conversion ratio of the starting 3,5-dichloro-1,4-dimethylpyrazole was 100% and a yield of 3,5-dichloro-1-methylpyrazole-4-carboxylic acid was 90.1%.

EXAMPLE 5

In the same manner as in Example 1 except for adding 7 mg (0.04 mmole) of ferrous oxalate as an iron compound, the reaction and operation were carried out.

A conversion ratio of the starting 3,5-dichloro-1,4-dimethylpyrazole was 95% and a yield of 3,5-dichloro-1-methylpyrazole-4-carboxylic acid was 93%.

EXAMPLE 6

In a 100 ml of an autoclave made of titanium were charged 50 ml of acetic acid, 6.5 g (50 mmole) of 5-chloro-1,4-dimethylpyrazole, 0.498 g (2 mmole) of cobalt acetate, 0.123 g (0.5 mmole) of manganese acetate and 0.408 g (4 mmole) of sodium bromide, and after supplying air therein to make 100 kg/cm2, reaction was carried at 140° C. for 2 hours. A conversion ratio of the starting 5-chloro-1,4-dimethylpyrazole was 100%. After removing acetic acid, the residue was esterified by diazomethane and the products were analyzed by a gas chromatography-mass spectrograph to obtain the result of M/e being 174 whereby it could be confirmed to be a methyl ester compound of the objective compound. As the result of the gas chromatography analysis, a yield of 5-chloro-1-methylpyrazole-4-carboxylic acid was 86.2%.

EXAMPLE 7

In a 100 ml of an autoclave made of Hasteroy C-276 were charged 50 ml of acetic acid, 4.8 g (50 mmole) of 1,4-dimethylpyrazole, 0.249 g (1 mmole) of cobalt acetate, 0.123 g (0.5 mmole) of manganese acetate and 0.204 g (2 mmole) of sodium bromide, and reaction and operation were carried out in the same manner as in Example 1.

A conversion ratio of the starting 1,4-dimethylpyrazole was 100% and a yield of 1-methylpyrazole-4-carboxylic acid was 87.7%.

EXAMPLE 8

In a 100 ml of an autoclave made of Hasteroy C-276 were charged 50 ml of acetio acid, 9.6 g (50 mmole) of 1-isopropyl-3-trifluoromethyl-5-methylpyrazole, 0.249 g (1 mmole) of cobalt acetate, 0.123 g (0.5 mmole) of manganese acetate and 0.204 g (2 mmole) of sodium bromide.

After supplying an oxygen gas in the autoclave to make 45 kg/cm2, the mixture was heated under stirring and reaction was carried out at 160° C. for 2 hours.

When the same operations were carried out as in Example 1, a conversion ratio of the starting 1-isopropyl-3-trifluoromethyl-5-methylpyrazole was 96.8% and a yield of 1-isopropyl-3-trifluoromethylpyrazole-5-carboxylic acid was 74.2%.

EXAMPLE 9

In a 100 ml of an autoclave made of Hasteroy C-276 were charged 50 ml of acetic acid, 8.2 g (50 mmole) of 1,5-dimethyl-3-trifluoromethylpyrazole, 0.249 g (1 mmole) of cobalt acetate, 0.123 g (0.5 mmole) of manganese acetate and 0.204 g (2 mmole) of sodium bromide, reaction and operation were carried out in the same manner as in Example 1.

A conversion ratio of the starting 1,5-dimethyl-3-trifluoromethylpyrazole was 96.8%, and a yield of 1-methyl-3-trifluoromethylpyrazole-5-carboxylic acid was 52.0%.

EXAMPLE 10

In a 100 ml of an autoclave made of Hasteroy C-276 were charged 50 ml of acetic acid, 10.5 g (50 mmole) of 3-chloro-1,4-dimethylpyrazole-5-sulfonamide, 0.249 g (1 mmole) of cobalt acetate, 0.0615 g (0.25 mmole) of manganese acetate and 0.204 g (2 mmole) of sodium bromide, reaction and operation were carried out in the same manner as in Example 1.

A conversion ratio of the starting 3-chloro-1,4-dimethylpyrazole-5-sulfonamide was 90%, and a yield of 3-chloro1-methyl-5-sulfonamidopyrazole-4-carboxylic acid was 75.5%.

EXAMPLE 11

In a 100 ml of an autoclave made of Hasteroy C-276 were charged 50 ml of acetic acid, 10.3 g (50 mmole) of 5-tertiarybutylthio-3-chloro-1,4-dimethylpyrazole, 0.249 g (1 mmole) of cobalt acetate, 0.0615 g (0.25 mmole) of manganese acetate and 0.204 g (2 mmole) of sodium bromide, reaction and operation were carried out in the same manner as in Example 1.

A conversion ratio of the starting 5-tertiarybutylthio-3-chloro-1,4-dimethylpyrazole was 74.5%, and a yield of 5-tertiarybutylthio-3-chloro-1-methylpyrazole-4-carboxylic acid was 52.2%.

We claim:

1. A process for preparing a pyrazolecarboxylic acid compound represented by the formula (II):

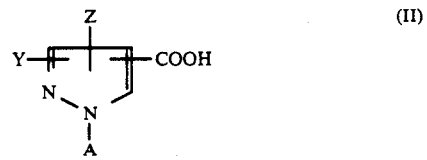

wherein Y and Z each represent a hydrogen atom, a halogen atom, a nitro group, a cyano group, $COOR_1$, $NR_1R_2$, $CONR_1R_2$, $SR_1$, $SO_2NR_1R_2$, $SO_2R_3$, $R_3CO$, $OR_4$, $CHX_2$ or $CX_3$; A represents a methyl group; where $R_1$ and $R_2$ each represent a hydrogen atom or an alkyl group having 1 to 10 carbon atoms; $R_3$ represents an alkyl group having 1 to 10 carbon atoms; $R_4$ represents a hydrogen atom, an alkyl group having 1 to 10 carbon atoms, a substituted or unsubstituted phenyl group, $CHF_2$, $CF_2$ or $CF_3CH_2$; and X represents a halogen atom which comprises oxidizing a pyrazole compound represented by the formula (I):

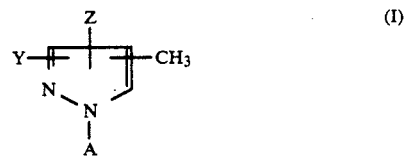

wherein Y, Z and A have the same meanings as defined above, by contacting said compound of the formula (I) with an oxygen-containing gas in the presence of a metal compound catalyst, at a temperature of 20° to 200° C. the partial pressure of said oxygen-containing gas being from atmospheric pressure to 80 kg/cm2 and the said metal compound catalyst is in an amount of 0.1 to 20 gram-atom based on 100 moles of the compound of the formula (I) and is at least one compound selected from the group consisting of iron compounds, cobalt compounds, nickel compounds, manganese compounds, cerium compounds and zirconium compounds.

2. The process for preparing a pyrazolecarboxylic acid compound according to claim 1, wherein said Y and Z are both chlorine atoms.

3. The process for preparing a pyrazolecarboxylic acid compound according to claim 1, wherein said oxygen-containing gas is pure oxygen gas or air.

4. The process for preparing a pyrazolecarboxylic acid compound according to claim 3, wherein the partial pressure of the oxygen-containing gas is from atmospheric pressure to 50 kg/cm$^2$.

5. The process for preparing a pyrazolecarboxylic acid compound according to claim 1, wherein said metal compound catalyst is at least one selected from the group consisting of cobalt compounds, manganese compounds and iron compounds.

6. The process for preparing a pyrazolecarboxylic acid compound according to claim 5, wherein said metal compound catalyst is (i) at least one cobalt compound and (i) at least one manganese compound which are selected from the group consisting of aliphatic acid cobalt salts, chelate compounds of cobalt, cobalt salts, aliphatic acid manganese salts, chelate compounds of manganese and manganese salts.

7. The process for preparing a pyrazolecarboxylic acid compound according to claim 6, wherein said cobalt compound and the manganese compound are selected from the group consisting of cobalt formate, cobalt acetate, cobalt octylate, cobalt acetylacetonate, cobalt chloride, cobalt bromide, cobalt iodide, cobalt carbonate, manganese formate, manganese acetate, manganese octylate, manganese acetylacetonate, manganese chloride, manganese bromide, manganese iodide and manganese carbonate.

8. The process for preparing a pyrazolecarboxylic acid compound according to claim 7, wherein said metal compound catalysts are cobalt acetate and manganese acetate.

9. The process for preparing a pyrazolecarboxylic acid compound according to claim 7, wherein the amount of manganese of said manganese compound to cobalt of said cobalt compound is 1 to 1/50 gram-atom.

10. The process for preparing a pyrazolecarboxylic acid compound according to claim 1, wherein a bromine compound is further added in the reaction system as a reaction promoter.

11. The process for preparing a pyrazolecarboxylic acid compound according to claim 10, wherein said bromine compound is selected from the group consisting of ammonium bromide, sodium bromide, potassium bromide, bromine and hydrobromide.

12. The process for preparing a pyrazolecarboxylic acid compound according to claim 11, wherein said bromine compound is sodium bromide.

13. The process for preparing a pyrazolecarboxylic acid compound according to claim 12, wherein the amount of said bromine compound is 0.5 to 20 moles based on 100 moles of the compound of the formula (I).

14. The process for preparing a pyrazolecarboxylic acid compound according to claim 1, wherein the reaction is carried out in the presence of a solvent.

15. The process for preparing a pyrazolecarboxylic acid compound according to claim 14, wherein the solvent is selected form the group consisting of a lower aliphatic acid or a lower aliphatic acid anhydride.

16. The process for preparing a pyrazolecarboxylic acid compound according to claim 15, wherein the solvent is selected from the group consisting of acetic acid, propionic acid, butyric acid, acetic anhydride and propionic anhydride.

17. The process for preparing a pyrazolecarboxylic acid compound according to claim 16, wherein the solvent is acetic acid.

18. The process for preparing a pyrazolecarboxylic acid compound according to claim 1, wherein the compound of the formula (I) is selected from the group consisting of 3,5-dichloro-1,4-dimethylpyrazole, 5-chloro-1,4-dimethylpyrazole, 1,4-dimethylpyrazole, 1,5-dimethyl-3-trifluoromethylpyrazole, 3-chloro-1,4-dimethylpyrazole-5-sulfonamide and 5-tertiarybutylthio-3-chloro-1,4-dimethylpyrazole.

19. The process for preparing a pyrazolecarboxylic acid compound according to claim 3, wherein the partial pressure of the oxygen-containing gas is from atmospheric pressure to 50 kg/cm$^2$; said metal compound catalyst is at least one cobalt compound, and one manganese compound and the amount of manganese of said manganese compound to cobalt of said cobalt compound if 1 to 1/50 gram-atom; a bromine compound is further added in the reaction system as a reaction promoter and the amount of said bromine compound is 0.5 to 20 moles based on 100 moles of the compound of the formula (I) and the reaction is carried out in the presence of a solvent.

20. The process for preparing a pyrazolecarboxylic acid compound according to claim 19, wherein said cobalt compound and the manganese compound are selected from the group consisting of cobalt formate, cobalt acetate, cobalt octylate, cobalt acetylacetonate, cobalt chloride, cobalt bromide, cobalt iodide, cobalt carbonate, manganese formate, manganese acetate, manganese octylate, manganese acetylacetonate, manganese chloride, manganese bromide, manganese iodide and manganese carbonate; said bromine compound is selected from the group consisting of ammonium bromide, sodium bromide, potassium bromide, bromine and hydrobromide; the solvent is selected from the group consisting of acetic acid, propionic acid, butyric acid, acetic anhydride and propionic anhydride; the amount of said metal compound catalyst is 1 to 10 gram-atom based on 100 moles of the compound of the formula (I) and the amount of manganese of said manganese compound to cobalt of said cobalt compound is 1 to 1.10 gram-atom.

21. The process for preparing a pyrazolecarboxylic acid compound according to claim 20, wherein said Y and Z are both chlorine atoms; said metal compound catalysts are cobalt acetate and manganese acetate; said bromine compound is sodium bromide and the solvent is acetic acid.

22. The process for preparing a pyrazolecarboxylic acid compound according to claim 21, wherein the compound of the formula (I) is selected from the group consisting of 3,5-dichloro-1,4-dimethylpyrazole, 5-chloro-1,4-dimethylpyrazole, 1,4-dimethylpyrazole, 1,5-dimethyl-3-trifluoromethylpyrazole, 3-chloro-1,4-dimethylpyrazole-5-sulfonamide and 5-tertiarybutylthio-3-chloro-1,4-dimethylpyrazole.

23. The process for preparing a pyrazolecarboxylic acid compound according to claim 20, wherein the compound of the formula (I) is 3,5-dichloro-1,4-dimethylpyrazole.

* * * * *

UNITED STATES PATENT AND TRADEMARK OFFICE
CERTIFICATE OF CORRECTION

PATENT NO. : 5,053,517
DATED : October 1, 1991
INVENTOR(S) : TAKIGAWA et al

It is certified that error appears in the above-identified patent and that said Letters Patent is hereby corrected as shown below:

Column 7, line 16 (Claim 6), change "(i)" to read --(ii)--.

Column 7, line 53 (Claim 13), change "claim 12" to read

--claim 11--.

Signed and Sealed this

Seventh Day of June, 1994

BRUCE LEHMAN

*Attest:*

*Attesting Officer*   Commissioner of Patents and Trademarks